(12) United States Patent
Bousquet et al.

(10) Patent No.: US 8,844,399 B2
(45) Date of Patent: Sep. 30, 2014

(54) ENDOSCOPE-LIKE ADJUSTABLE STRUCTURE

(75) Inventors: Sadia Bousquet, Moissy Cramayel Cedex (FR); Patrick Gaisnon, Moissy Cramayel Cedex (FR); Sylvie Mozer, Moissy Cramayel Cedex (FR); Jerome Szewczyk, Vienne en Arthies (FR)

(73) Assignee: SNECMA, Paris (FR)

( * ) Notice: Subject to any disclaimer, the term of this patent is extended or adjusted under 35 U.S.C. 154(b) by 180 days.

(21) Appl. No.: 13/517,096

(22) PCT Filed: Jan. 12, 2011

(86) PCT No.: PCT/FR2011/050054
§ 371 (c)(1),
(2), (4) Date: Jun. 19, 2012

(87) PCT Pub. No.: WO2011/086324
PCT Pub. Date: Jul. 21, 2011

(65) Prior Publication Data
US 2012/0291583 A1    Nov. 22, 2012

(30) Foreign Application Priority Data
Jan. 14, 2010    (FR) ..................................... 10 00139

(51) Int. Cl.
| | | |
|---|---|---|
| *B25J 17/00* | (2006.01) | |
| *B25J 17/02* | (2006.01) | |
| *B25J 18/00* | (2006.01) | |
| *H04N 13/00* | (2006.01) | |
| *A61B 1/04* | (2006.01) | |
| *G01N 29/22* | (2006.01) | |
| *F01D 21/00* | (2006.01) | |

(52) U.S. Cl.
CPC ............ *F01D 21/003* (2013.01); *G01N 29/225* (2013.01); *F05D 2260/80* (2013.01)
USPC ........................................ 74/490.04; 348/45

(58) Field of Classification Search
CPC ............... A61B 1/00071; A61B 1/005; A61B 2017/003; A61B 2017/00323; A61B 2017/2905; A61B 2017/2927; A61B 1/0057; A61B 2019/2242; A61B 17/1631; B25J 9/104; B25J 18/06
USPC ........... 74/490.04; 348/45; 600/139, 140, 141
See application file for complete search history.

(56) References Cited

U.S. PATENT DOCUMENTS

| | | | | |
|---|---|---|---|---|
| 4,930,494 A | * | 6/1990 | Takehana et al. | ............. 600/145 |
| 5,531,664 A | * | 7/1996 | Adachi et al. | ................. 600/149 |

(Continued)

FOREIGN PATENT DOCUMENTS

| | | |
|---|---|---|
| EP | 2 042 076 | 4/2009 |
| EP | 2 119 875 | 11/2009 |

OTHER PUBLICATIONS

International Search Report Issued Oct. 28, 2011 in PCT/FR11/50054 Filed Jan. 12, 2011.

*Primary Examiner* — Justin Krause
(74) *Attorney, Agent, or Firm* — Oblon, Spivak, McClelland, Maier & Neustadt, L.L.P.

(57) ABSTRACT

A flexible and steerable structure for non-destructive inspection, the structure including a longitudinal body and at least one actuator enabling the curvature of at least a portion of the longitudinal body to be modified, the actuator being carried by a support associated with the longitudinal body and including a distal portion that is spaced apart or that is spaceable apart from the longitudinal body and that is connected to a portion of the longitudinal body by a traction line.

17 Claims, 2 Drawing Sheets

(56) References Cited

U.S. PATENT DOCUMENTS

| | | |
|---|---|---|
| 8,046,049 B2 * | 10/2011 | Govari et al. ................. 600/424 |
| 2003/0092965 A1 | 5/2003 | Konomura et al. |
| 2004/0019252 A1 | 1/2004 | Hirata |
| 2008/0065107 A1 * | 3/2008 | Larkin et al. .................. 606/130 |
| 2009/0079821 A1 | 3/2009 | Bousquet et al. |
| 2009/0278924 A1 | 11/2009 | Heyworth et al. |
| 2011/0082538 A1 * | 4/2011 | Dahlgren et al. ............ 623/2.11 |
| 2012/0123326 A1 * | 5/2012 | Christian et al. ........... 604/95.03 |

\* cited by examiner

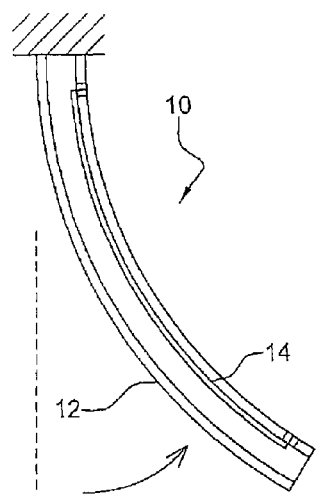
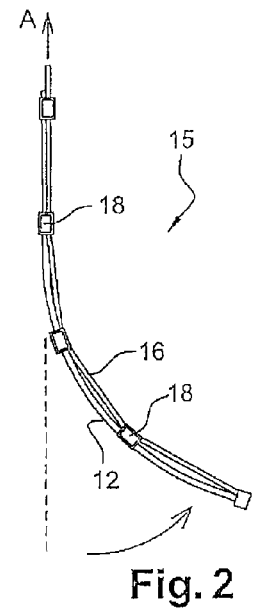
Fig. 1     Fig. 2
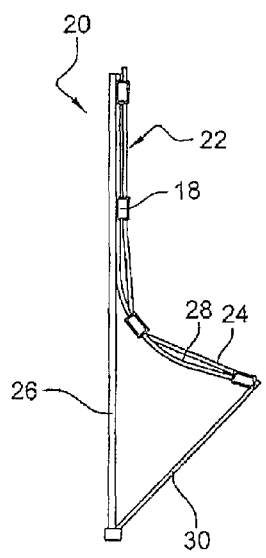
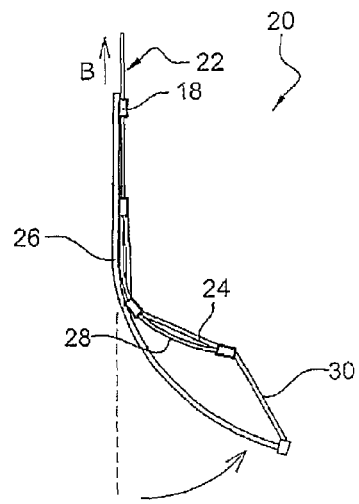
Fig. 3     Fig. 4

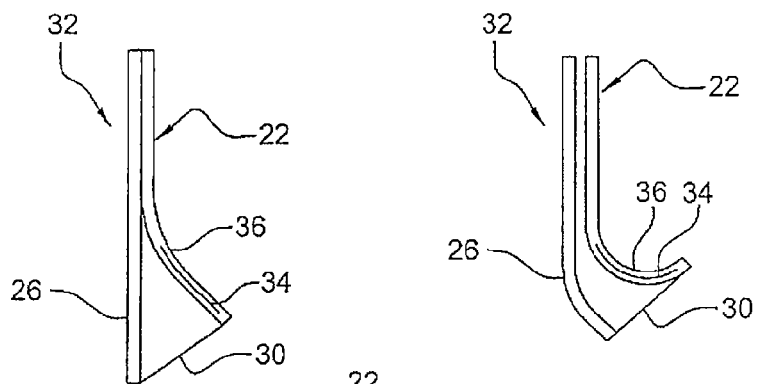
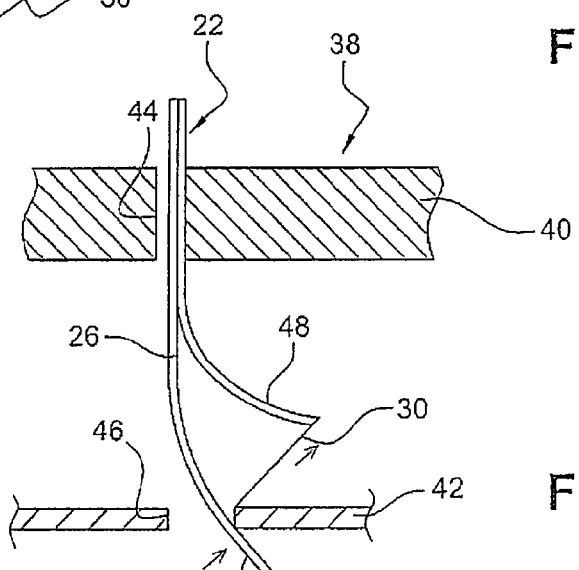
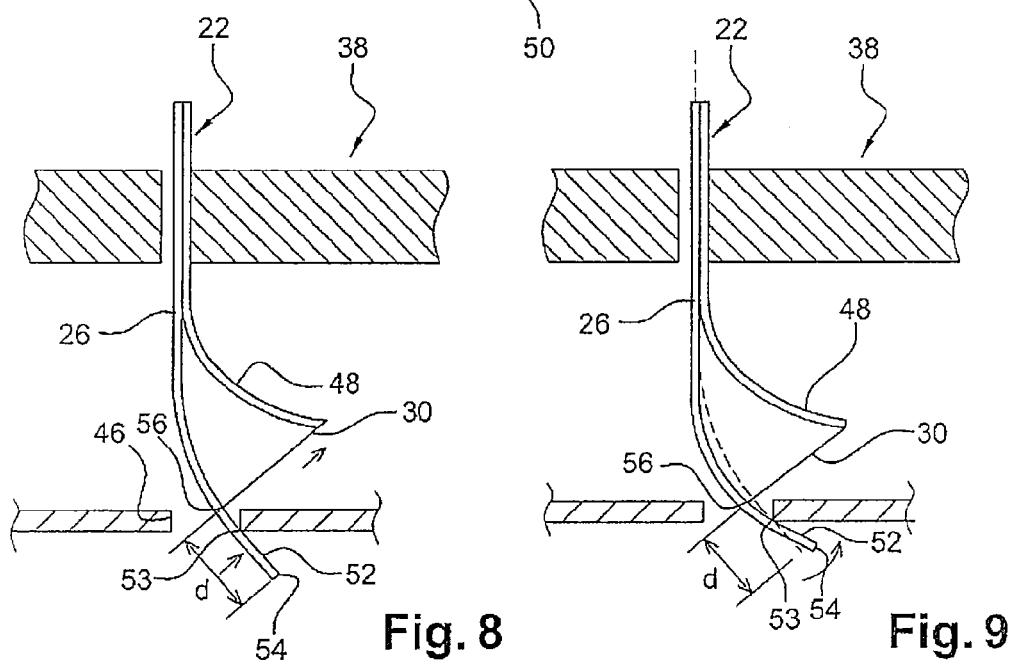

ENDOSCOPE-LIKE ADJUSTABLE STRUCTURE

The present invention relates to a flexible and steerable structure for inspecting the inside of a mechanical system, such as a turbine engine, for example, in particular by means of a sensor of the eddy current or ultrasound type.

Certain present flexible and steerable structures such as an endoscope or a support for a non-destructive inspection probe are in the form of a long tube that is rigid or elastically deformable and that has an end that is steerable relative to its longitudinal axis in order to select a particular positioning angle and in order to make it easier to cause the endoscope or the probe support to advance.

In order to curve a particular zone of the endoscope in appropriate manner, proposals have already been made to place mechanical actuators along the structure, such as traction lines or indeed lines made of shape-memory material. Those actuators are shortened by applying traction, or by the effect of an increase in temperature, thereby causing the curvature of the endoscope to be modified in the zones in which the actuators are located.

Nevertheless, that type of device suffers from limitations due mainly to lack of mobility and maneuverability in spaces that are geometrically complex or confined. Furthermore, it also presents drawbacks in terms of capacity to curve the end of the endoscope.

In order to solve that difficulty, the Applicant has made proposals in its patent application FR 07/06726, to mount the actuator on a portion of the longitudinal body of the device that presents varying rigidity so as to obtain a small amount of flexing in zones where the rigidity is large and a greater amount of flexing in zones where the rigidity is smaller, so as to arrive at a profile for the device that is of varying curvature.

Nevertheless, the curvatures that can be obtained with devices of that type or of the other types described above remain limited, thereby restricting their options in use.

Furthermore, in certain situations when inspecting a turbine engine it can be desirable to achieve stable and reliable attachment of the device on stationary portions of the engine in order to perform non-destructive inspection and/or in order to limit the effect of gravity on the device as a whole while continuing to inspect the engine.

A particular object of the invention is to provide a solution to those problems that is inexpensive and effective, making it possible to avoid the drawbacks of the prior art.

To this end, the invention provides a flexible and steerable structure for non-destructive inspection, the structure comprising a longitudinal body and at least one actuator enabling the curvature of at least a portion of the longitudinal body to be modified, the structure being characterized in that the actuator is carried by a support associated with the longitudinal body and having a distal portion that is spaced apart or that is spaceable apart from the longitudinal body and that is connected to a portion of the longitudinal body by a traction line.

Unlike the prior art, the invention no longer proposes arranging the actuator along the longitudinal body, but rather proposes assembling it on a support that is spaced apart therefrom.

In this configuration, the support forms a lever arm making it easier to flex the longitudinal body, with flexing being performed by means of a force that acts laterally relative to the longitudinal body along the traction line, as opposed to along the longitudinal body, thereby making it possible to increase the amount of flexing of the longitudinal body.

The transmission ratio, i.e. the ratio between the flexing angle and the shortening of the actuator is smaller than in the prior art. This makes it possible to achieve much more accurate positioning of the flexed portion of the longitudinal body.

The force that results from operating the actuator is better transmitted to the longitudinal body. This good force transmission makes it possible to achieve stable attachment of the flexible structure by flexing and pressing a portion of the longitudinal body against a stationary portion of a three-dimensional structure that is to be explored. It is thus possible to guarantee that a non-destructive inspection sensor placed at the distal end of the longitudinal body is in a static position when performing a non-destructive inspection operation.

In the aviation industry, the invention thus makes it possible to explore zones of a turbine engine that were previously inaccessible without disassembling the engine, thereby contributing to reducing down time and costs.

According to another characteristic of the invention, the actuator is made of shape-memory material.

In a variant, the actuator may be mechanical and comprise a cable connected directly to the traction line of the longitudinal body and it may extend along the distal portion of the support.

The distal portion of the support may be rigid, and under such circumstances the actuator may be a cable as described above.

In a variant, the distal portion of the support may be deformable, and under such circumstances the actuator may comprise a shape-memory material that, on contracting, causes the distal portion of the support to deform and induces traction on the line connected to the longitudinal body.

In an embodiment of the invention, the traction line of the longitudinal body is connected thereto at a distance from its distal end in a zone that is to press with point or quasi-point contact against a stationary element of the structure for inspection in order to form a pivot point.

The pivot point is situated between the distal end of the longitudinal body and the point where the traction line is connected to the longitudinal body. As a result, it is possible to cause the distal end of the longitudinal body to perform an angular scan, and this can be of use when it is desired to view a certain angular extent of the inside of the structure under inspection on a continuous basis.

In a variant, the traction line is connected to the distal end of the longitudinal body or to the vicinity of said distal end.

Advantageously, the non-destructive inspection means mounted at the distal end of the longitudinal body are constituted, for example, by eddy current probes or by ultrasound probes.

In a practical embodiment of the invention, the traction line is a metal wire.

The longitudinal body may also include at least one portion that is fitted with at least one actuator, of the mechanical or shape-memory material type, in order to provide additional flexing of the longitudinal body.

The invention can be better understood and other details, advantages, and characteristics of the invention appear on reading the following description made by way of non-limiting example and with reference to the accompanying drawings, in which:

FIGS. 1 and 2 are diagrammatic axial section views of two flexible and steerable structures of the prior art;

FIG. 3 is a diagrammatic axial section view of a flexible and steerable structure of the invention;

FIG. 4 is a diagrammatic axial section view of the FIG. 3 flexible and steerable structure in a curved position;

FIG. 5 is a diagrammatic axial section view of a flexible and steerable structure in another embodiment of the invention;

FIG. 6 is a diagrammatic axial section view of the FIG. 5 flexible and steerable structure in a curved position;

FIG. 7 is a diagrammatic axial section view in the attachment position of a flexible and steerable structure of the invention;

FIG. 8 is a diagrammatic axial section view of a flexible and steerable structure of the invention pressing against a stationary structure that is to be explored; and FIG. 9 is a diagrammatic view showing the movement of the FIG. 8 flexible and steerable structure.

Reference is made initially to FIG. 1 which shows a flexible and steerable structure 10 for non-destructive inspection of the prior art, the structure comprising a longitudinal body 12 fitted with an actuator 14 of shape-memory material arranged along the longitudinal body 12 and inside it. By way of example, the actuator 14 is in the form of a line connected to electrical power supply means enabling the line to be heated by the Joule effect. Heating the line 14 causes it to contract, thereby causing the longitudinal body 12 to flex.

FIG. 2 shows a steerable and flexible structure 15 similar to that of FIG. 1, except that the actuator is a metal wire 16 extending along the longitudinal body 12 to the distal end of the longitudinal body 12. The line 16 is held along the longitudinal body 12 by means of a plurality of hollow guides 18 that are fastened to the longitudinal body 12. With this type of control structure, traction (arrow A) applied to the proximal end of the line 16 leads to the distal end of the longitudinal body 12 flexing.

Those structures 10 and 15 do not enable the flexed portion of the longitudinal body 12 to flex through a large angle or to be positioned accurately. Furthermore, they do not enable the inspection structure to be attached in stable and static manner to a nearby stationary portion of a mechanical structure for inspection, with this being for the reasons set out in detail above.

The invention proposes associating the flexible and steerable structure 20 with a support 22 having a distal portion 24 that is spaced apart or spaceable apart from the longitudinal body 26 and that carries an actuator 28, this distal portion 24 being connected to the longitudinal body 26 by a traction line 30.

In an embodiment of the invention shown in FIGS. 3 and 4, the distal portion 24 is rigid. The actuator 28 is a cable that extends along the support 22 in hollow guides 18 fastened to the support 22. At the end of the distal portion 24 of the support 22, the actuator 28 is connected directly to the traction line 30 that is connected to the distal end of the longitudinal body 26.

Traction (arrow B) applied to the proximal end of the cable 28 causes the distal end of the longitudinal body 26 to flex, with the support 22 remaining stationary during this operation (FIG. 4).

In another embodiment of the invention as shown in FIGS. 5 and 6, the flexible and steerable structure 32 comprises an actuator 34 in the form of a line of shape-memory material incorporated in the distal portion 36 of the support 22, which support is deformable. The distal portion 36 is connected to the longitudinal body 26 by a traction line 30.

Heating the line of shape-memory material leads to the line contracting, thereby causing the distal portion 36 of the support 22 to flex, and thus flexing the longitudinal body 26 (FIG. 6).

In the two above-described embodiments, the longitudinal body 26 may be made of a material that is elastically deformable, thereby enabling it to return to its rest position (FIGS. 3 and 5) when the traction cable 28 is relaxed, or when ceasing to heat the line 34 of shape-memory material.

The distal portion 24, 36 of the support 22 constitutes a lever arm for flexing the longitudinal body 26, thereby enabling the flexed portion of the longitudinal body 26 to be positioned accurately because of a transmission ratio (i.e. the bending angle divided by the shortening of the actuator) that is smaller than in the prior art. Thus, for a given flexing angle of the longitudinal body 26, it is necessary for the length of the actuator 28, 34 to shorten more than in the prior art.

FIG. 7 is an axial section view of a structure 38 for inspection that has two walls 40 and 42 that are spaced apart from each other and that include two openings 44 and 46 for passing a flexible and steerable structure of the invention.

In the configuration shown in this figure, the traction line 30 is connected to the distal end of the longitudinal body 26. The longitudinal body 26 is inserted through the two openings 44 and 46 and the support 22 is inserted in the first opening so that its distal portion 48 is situated between the two walls 40 and 42. Controlling the actuator of the distal portion 48 causes the longitudinal body 26 to flex and brings the distal end 50 of the longitudinal body 26 to bear against the edge of the second opening. Furthermore, a portion of the traction line 30 in the immediate proximity of the longitudinal body is pressed against the inside surface of the second opening 46 during flexing of the longitudinal body 26.

In this way, the longitudinal body 26 is positioned in static and stable manner against the second wall 42. The stability of this positioning is increased with increasing pressure force applied laterally to the longitudinal body 26 from the spaced-apart distal portion 48. This transmission of force from the actuator by the traction line 30 is particularly large for small amounts of flexing, preferably less than 30°.

FIG. 8 shows a structure 38 for inspection that is similar to that of FIG. 7. The traction line 30 is connected to the longitudinal body 26 at a distance d from its distal end 54. The longitudinal body 26 is inserted inside the second opening 46 in such a manner that, during flexing, its end portion 52 comes to press with point or almost point contact against an edge of the second opening (FIG. 8).

This configuration enables a pivot point 53 to be established between the distal end 54 of the longitudinal body 26 and the point 56 where the traction line 30 is connected to the longitudinal body 26.

When the longitudinal body 26 is elastically deformable, repeated operation of the actuator carried by the distal portion 48 of the support 22 enables the distal end of the longitudinal body 26 to perform an angular scan.

Since the actuator that enables angular scanning to be performed can be the same actuator as the actuator that is used for the initial flexing (FIG. 8) of the longitudinal body when using a mechanical actuator such as a cable, continued application of traction causes the distal end of the longitudinal body 26 to pivot. When the initial flexing (FIG. 8) is performed using a line of shape-memory material, a second line that is also made of shape-memory material may be incorporated in the distal portion 48 of the support 22, and repeated operation of this second line enables the distal end 54 of the longitudinal body 26 to be caused to perform an angular scan.

A flexible and steerable structure 20, 32 is engaged in a mechanical structure of the type shown in FIGS. 7 and 8 initially by inserting the non-curved longitudinal body 26 through the first and second openings 44 and 46. The support 22 is also inserted through the first opening 44 by pivoting movement and then by movement in translation, and the traction line 30 is then put under tension so as to place the structure 20, 32 in a ready position as shown in FIGS. 3 and 5.

Non-destructive inspection means (not shown) may be mounted at the distal end of the longitudinal body 26. By way of example, such means may be eddy current probes or ultrasound probes.

In other variants of the invention, the flexible structure 20, 32 includes at least one mechanical actuator 16 or shape-memory material actuator 14 incorporated in the longitudinal body 26.

The invention claimed is:

1. A flexible and steerable structure for non-destructive inspection, the structure comprising:
    a support;
    a longitudinal body; and
    at least one actuator enabling curvature of at least a portion of the longitudinal body to be modified,
    wherein the at least one actuator is carried by the support associated with the longitudinal body,
    wherein the support includes a distal portion that is configured to be spaced apart from the longitudinal body, and the distal portion of the support is connected to a portion of the longitudinal body by a traction line, the traction line being different than the actuator.

2. A structure according to claim 1, wherein the at least one actuator is made of shape-memory material.

3. A structure according to claim 1, wherein the at least one actuator is mechanical.

4. A structure according to claim 1, wherein the at least one actuator comprises a cable that is connected directly to the traction line of the longitudinal body and that extends along the distal portion of the support.

5. A structure according to claim 4, wherein the distal portion is rigid.

6. A structure according to claim 1, wherein the traction line of the longitudinal body is connected thereto at a distance from its distal end.

7. A structure according to claim 1, wherein the traction line is connected to the distal end of the longitudinal body or to a vicinity of the distal end.

8. A structure according to claim 1, wherein the distal end of the longitudinal body includes non-destruction inspection means, or an eddy current or ultrasound probes.

9. A structure according to claim 1, wherein the traction line is a metal wire.

10. A structure according to claim 1, wherein the longitudinal body includes at least one portion that is fitted with at least one of a mechanical actuator or a shape-memory material actuator.

11. A flexible and steerable structure for non-destructive inspection, the structure comprising:
    a support;
    a longitudinal body provided with inspection means at a distal portion; and
    at least one actuator enabling the curvature of at least a portion of the longitudinal body to be modified,
    wherein the at least one actuator is formed outside the longitudinal body, and is carried by the support of longitudinal shape formed outside the longitudinal body and related thereto, said support having a distal portion that is configured to be laterally spaced apart from the longitudinal body, said support being further connected from its distal portion to a portion of the longitudinal body by a traction line.

12. A structure according to claim 11, wherein the distal portion of the support is spaced apart from the longitudinal body at a greater distance than a proximal portion of the support.

13. A structure according to claim 4, wherein the distal portion is deformable.

14. A structure according to claim 1, wherein the at least one actuator extends through a plurality of hollow guides along a length of the support, the hollow guides being fastened to the support.

15. A structure according to claim 1, wherein the distal portion of the support is configured to be laterally spaced apart from the longitudinal body in response to movement of the actuator.

16. A structure according to claim 11, wherein the distal portion of the support is configured to be laterally spaced apart from the longitudinal body in response to movement of the actuator.

17. A flexible and steerable structure for non-destructive inspection, the structure comprising:
    a support;
    a longitudinal body; and
    at least one actuator enabling curvature of at least a portion of the longitudinal body to be modified,
    wherein the at least one actuator is carried by the support associated with the longitudinal body,
    wherein the support includes a distal portion that is spaceable apart from the longitudinal body, and the distal portion of the support is connected to a portion of the longitudinal body by a traction line, the traction line being different than the actuator.

* * * * *